United States Patent [19]

Erskine

[11] Patent Number: 5,690,619
[45] Date of Patent: Nov. 25, 1997

[54] CATHETER-ADVANCEMENT ACTUATED NEEDLE RETRACTION SYSTEM

[75] Inventor: Timothy J. Erskine, Sandy, Utah

[73] Assignee: Becton Dickinson and Company, Franklin Lakes, N.J.

[21] Appl. No.: 736,616

[22] Filed: Oct. 24, 1996

Related U.S. Application Data

[63] Continuation of Ser. No. 581,390, Dec. 29, 1995, abandoned, which is a continuation of Ser. No. 400,150, Mar. 7, 1995, abandoned.

[51] Int. Cl.[6] ................................................ A61M 5/00
[52] U.S. Cl. ........................ 604/263; 604/164; 604/165
[58] Field of Search ................................ 604/263, 164, 604/165, 168, 171, 187, 192, 197, 198, 272, 110

[56] References Cited

U.S. PATENT DOCUMENTS

| | | |
|---|---|---|
| 4,747,831 | 5/1988 | Kulli . |
| 4,834,718 | 5/1989 | McDonald ............................. 604/195 |
| 4,904,242 | 2/1990 | Kulli . |
| 4,927,414 | 5/1990 | Kulli . |
| 4,973,316 | 11/1990 | Dysarz . |
| 4,978,344 | 12/1990 | Dombrowski et al. . |
| 4,994,034 | 2/1991 | Botich et al. ............................ 604/110 |
| 4,994,041 | 2/1991 | Dombrowski et al. . |
| 4,994,042 | 2/1991 | Vadher . |
| 5,104,384 | 4/1992 | Parry . |
| 5,125,414 | 6/1992 | Dysarz . |
| 5,129,884 | 7/1992 | Dysarz . |
| 5,137,519 | 8/1992 | Littrell et al. ............................ 604/174 |
| 5,279,590 | 1/1994 | Sinko et al. ............................ 604/263 |
| 5,300,045 | 4/1994 | Plassche, Jr. ............................ 604/263 |
| 5,306,253 | 4/1994 | Brimhall ................................. 604/165 |
| 5,312,361 | 5/1994 | Zadini et al. . |
| 5,376,075 | 12/1994 | Haughton et al. . |
| 5,395,337 | 3/1995 | Clemens et al. ......................... 604/110 |
| 5,407,431 | 4/1995 | Botich et al. . |
| 5,411,486 | 5/1995 | Zadini et al. . |
| 5,501,675 | 3/1996 | Erskine ................................. 604/263 |

FOREIGN PATENT DOCUMENTS

| | | |
|---|---|---|
| 41 40 099 C1 | 5/1993 | Germany . |
| 2 088 721 | 6/1982 | United Kingdom . |
| WO 94/21319 | 9/1994 | WIPO . |
| WO 95/23003 | 8/1995 | WIPO . |

Primary Examiner—Michael Powell Buiz
Assistant Examiner—N. Kent Gring
Attorney, Agent, or Firm—Eric M. Lee

[57] ABSTRACT

A catheter-advancement actuated needle retraction system is disclosed herein. The invention includes a generally hollow barrel that houses a needle hub, which can include a flashback chamber. A needle is affixed to the distal end of the needle hub and is aligned to extend through an opening in the distal end of the barrel. The needle extends through a catheter hub and catheter affixed to the catheter hub. A spring is disposed in the barrel lumen to cooperate with the needle hub to urge the needle hub toward the proximal end of the barrel. A latch actuator is releasably engaged with the catheter hub. A latch which cooperates with the latch actuator is movable between one position which maintains the needle hub adjacent to the distal end of the barrel and a second position allowing the spring to urge the needle hub to the proximal end of the barrel. A mechanism may be provided to cushion the needle hub as it contacts the proximal end of the barrel by the force of the spring.

4 Claims, 16 Drawing Sheets

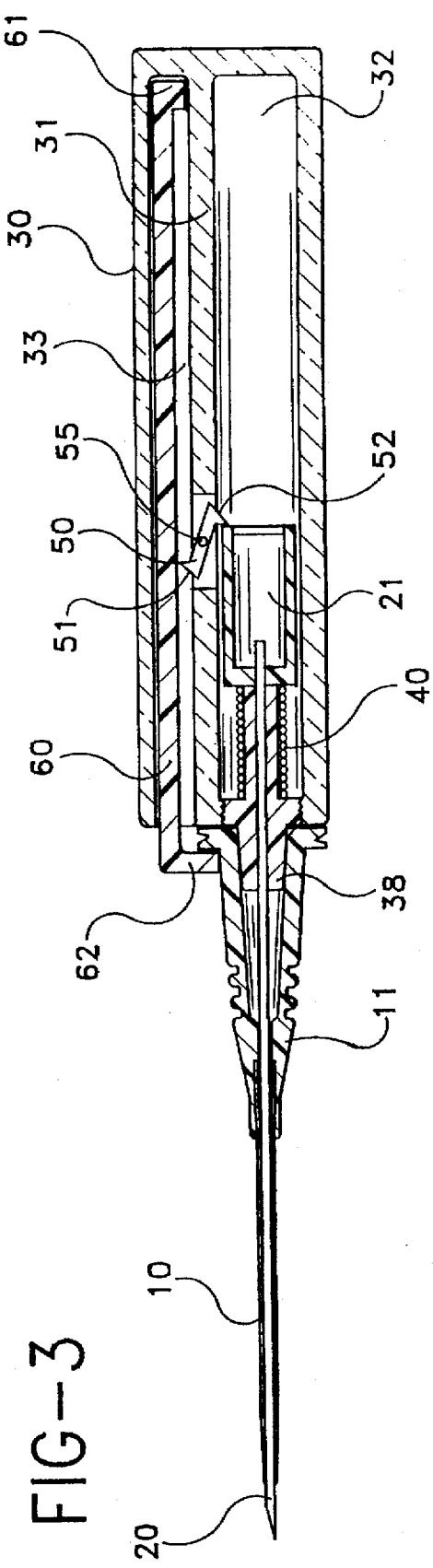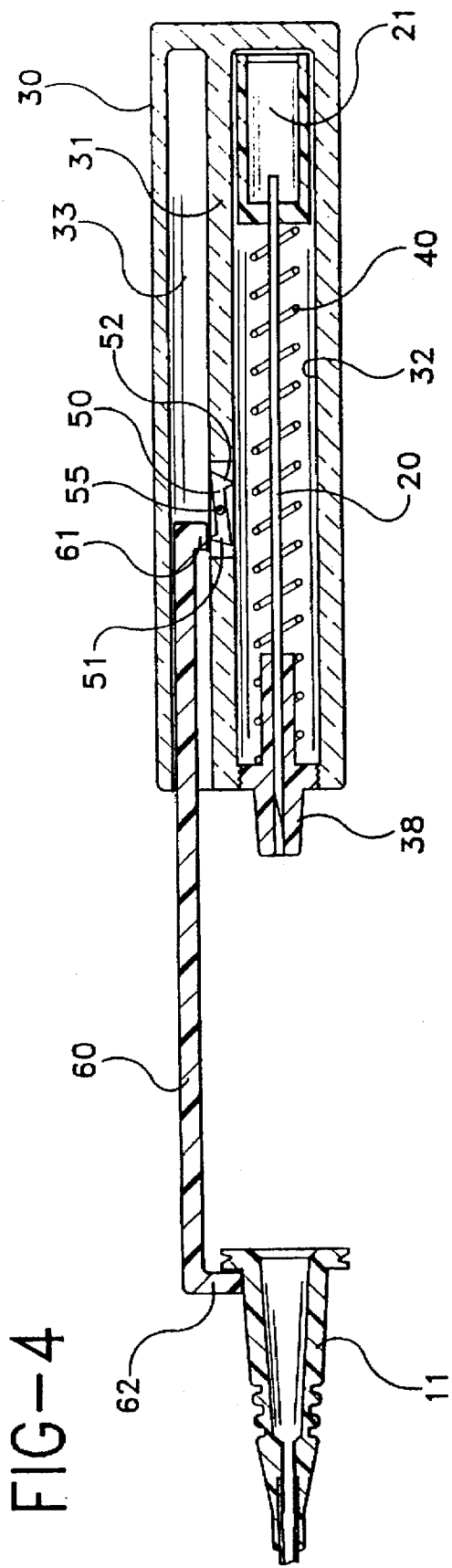

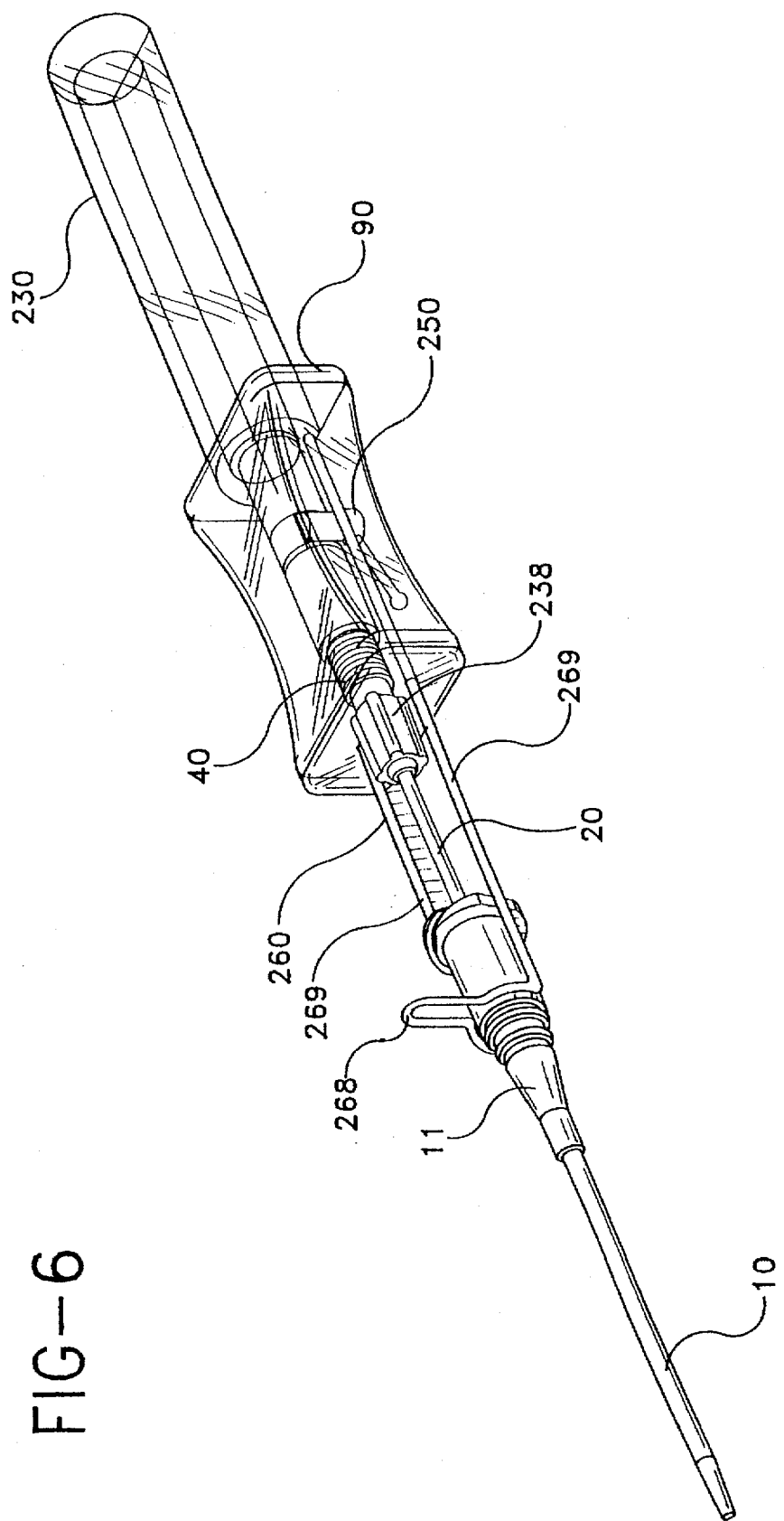

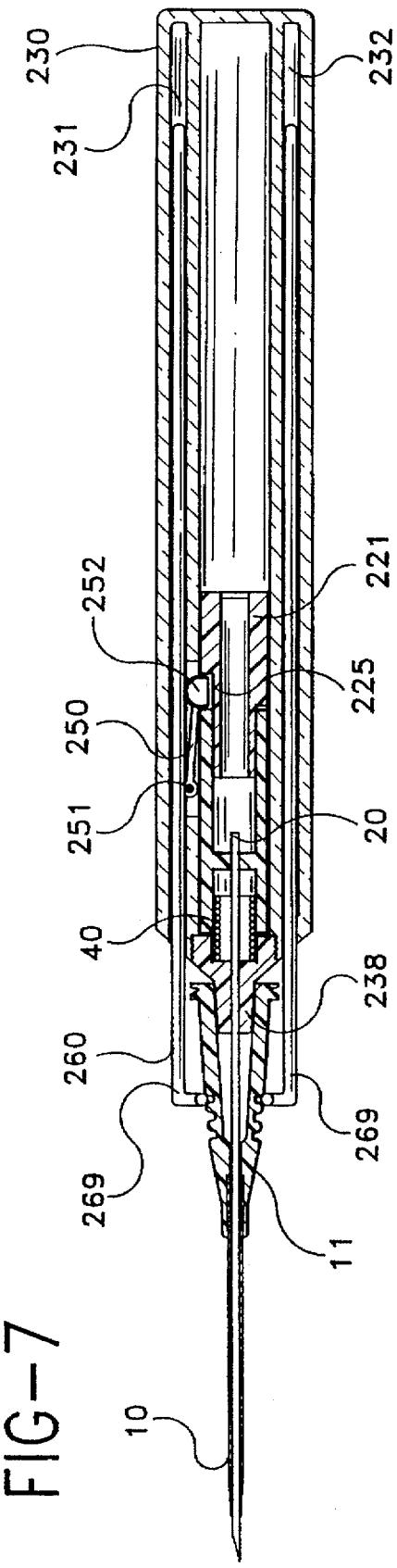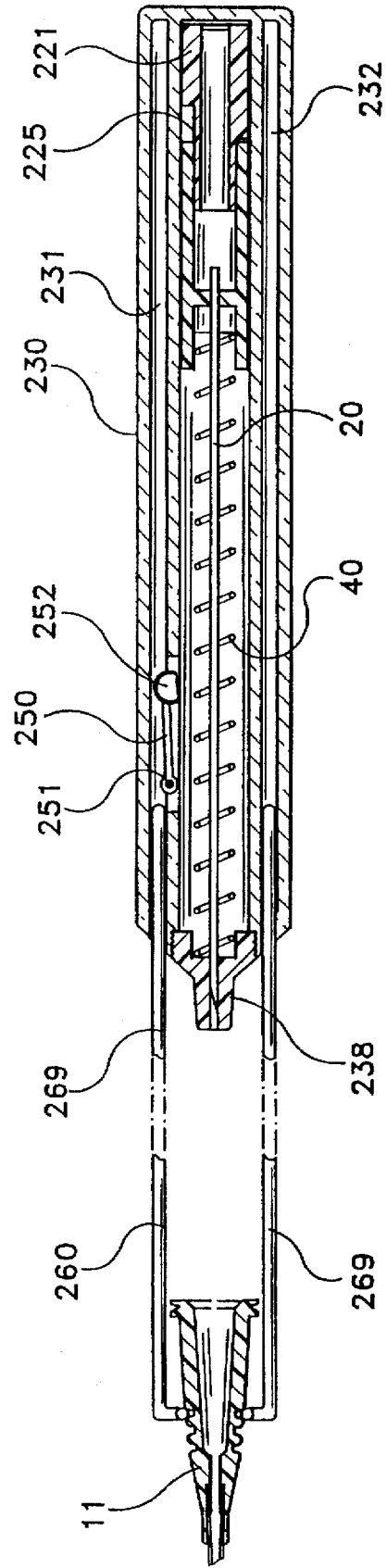

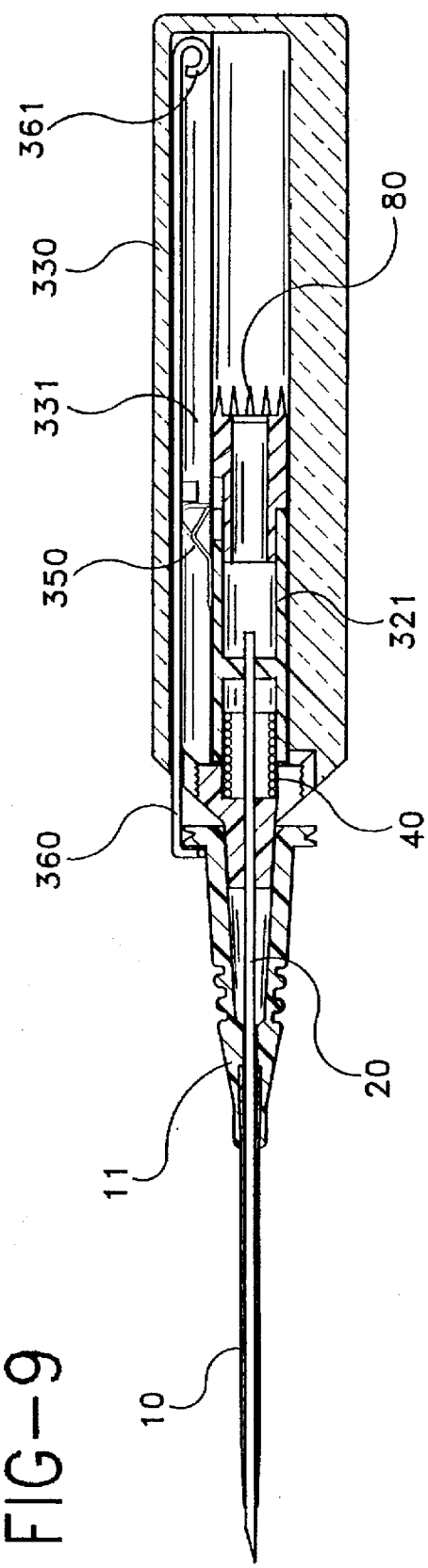
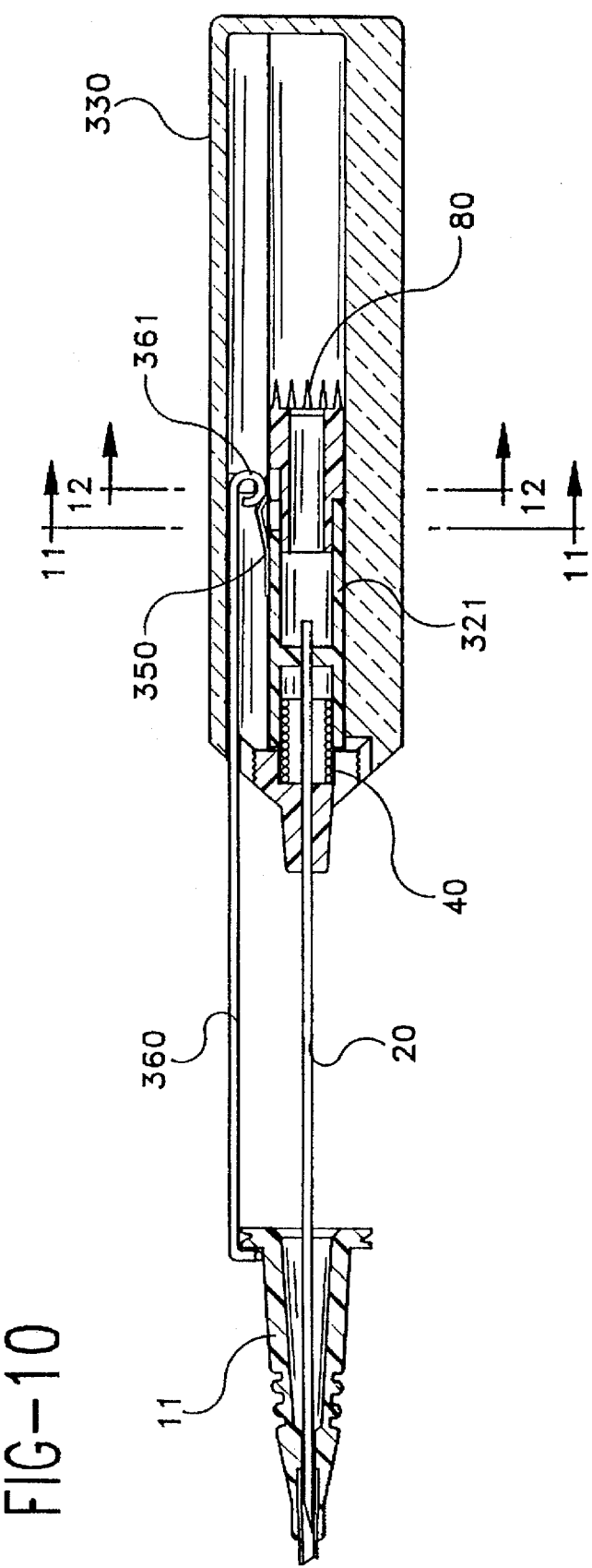

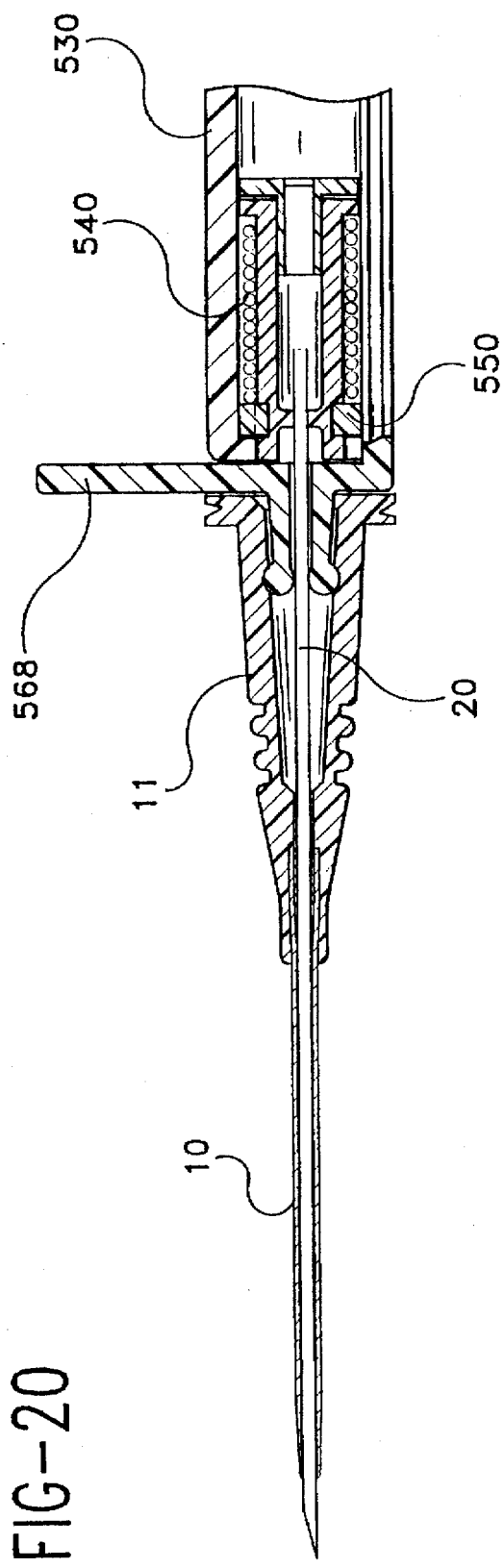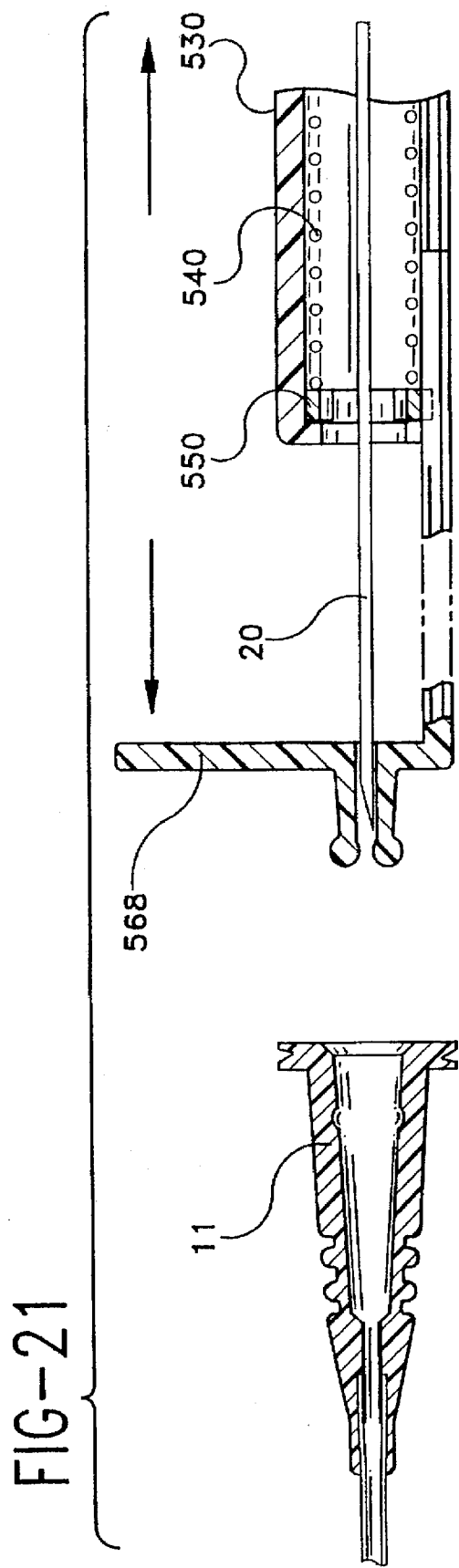

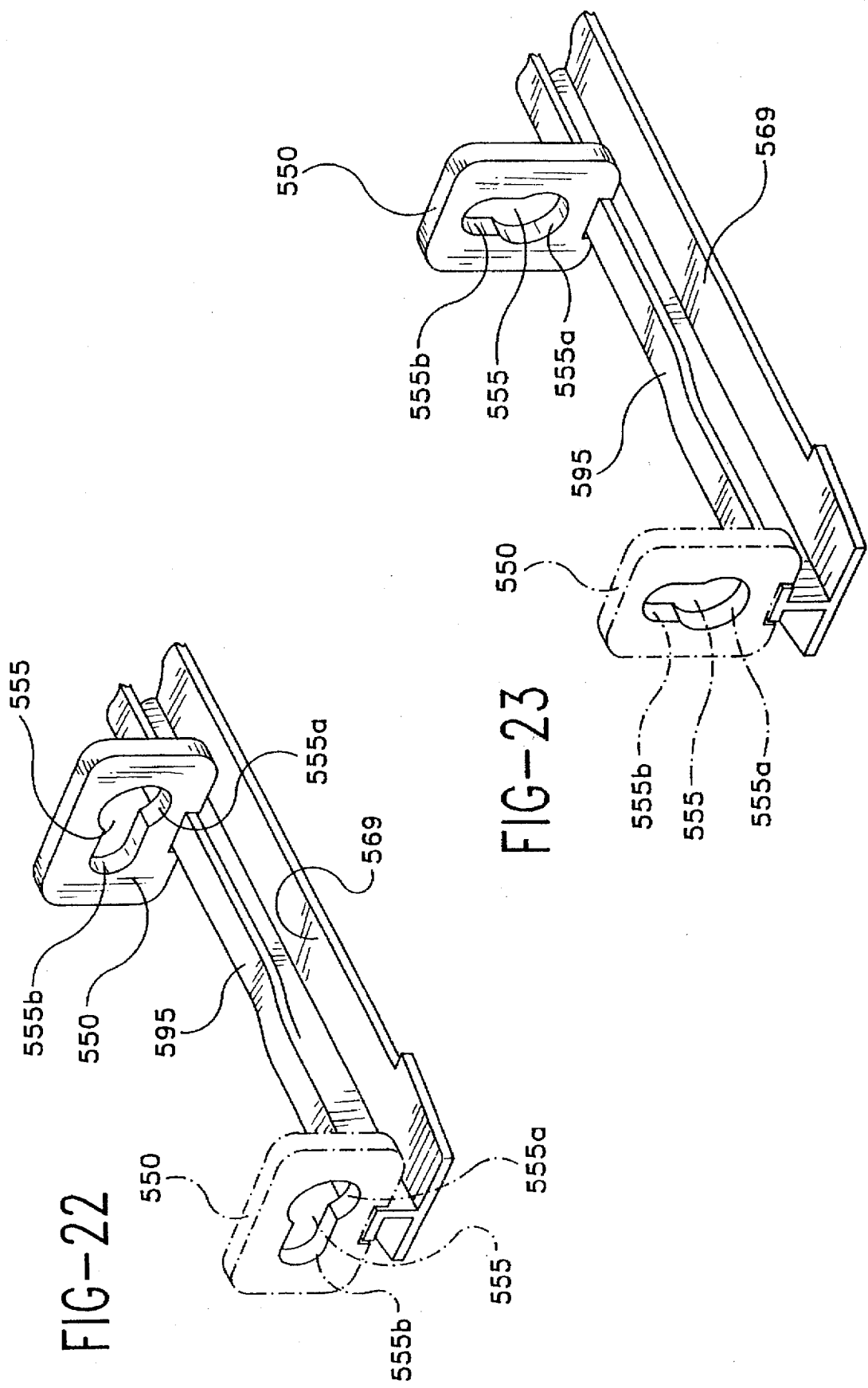

CATHETER-ADVANCEMENT ACTUATED NEEDLE RETRACTION SYSTEM

This application is a continuation of application Ser. No. 08/581,390, filed Dec. 29, 1995, now abandoned, which is a continuation of application Ser. No. 08/400,150, filed Mar. 7, 1995, now abandoned.

BACKGROUND OF THE INVENTION

This invention relates in general to an intravenous ("IV") catheter and introducer needle assembly having a novel needle retraction system.

IV catheters are used to provide fluid to or withdraw fluid from a patient. In order to properly place an IV catheter in a patient's vein, a sharp introducer needle must be used to puncture the skin, tissue and vein wall to provide a path for placement of the catheter in the vein. Typical IV catheters are "over-the-needle" catheters where the catheter is coaxially placed over the needle. The catheter thus rides with the needle through the skin, tissue and vein wall and into the patient's vein. When the needle pierces the vein, blood will "flashback" into the needle. Thus, once the medical technician observes this "flashback" of blood, the medical technician will know that the catheter and needle have been inserted in the vein. The needle can then be withdrawn from the patient and the catheter can be advanced further into the vein.

In recent years, there has been great concern over the immediate disposal of needles after use. This concern has arisen because of the advent of currently incurable and fatal diseases, such as Acquired Immune Deficiency Syndrome ("AIDS"), which can be transmitted by the exchange of body fluids from an infected person to another person. If a needle has been used to place a catheter in the vein of an AIDS infected person, the needle is a vehicle for the transmission of the disease. Thus, it is extremely important for a medical technician to properly dispose of tile needle to avoid a needlestick with the contaminated needle. Unfortunately in certain medical environments, such as emergency situations, needlesticks with a contaminated needle can occur if the contaminated needle is not somehow covered immediately after use.

SUMMARY OF THE INVENTION

It is therefore an object of this invention to provide a safety catheter and needle introducer assembly where the needle can be covered immediately after use.

It is another object of this invention to provide a safety catheter and needle introducer assembly that is easy to use.

The catheter-advancement actuated needle retraction system of the invention comprises a generally hollow barrel, a needle slidably disposed in the barrel so the sharp distal tip of the needle can initially extend beyond the distal end of the barrel and then can be retracted completely into the barrel, a needle hub, which may include a flashback chamber, fixed to the proximal end of the needle, a spring associated with the needle hub and the barrel, a movable latch for initially maintaining the needle hub adjacent to the distal end of the barrel, and an actuation device that can cooperate with the latch to allow the spring to force the needle hub and the needle toward the proximal end of the barrel.

The above and other objects and advantages of the invention will be apparent upon consideration of the drawings and the following detailed description.

BRIEF DESCRIPTION OF THE DRAWINGS

The preferred embodiments are illustrated in the drawings in which like reference numerals refer to like elements and in which:

FIG. 3 is a side view in cross-section of the first embodiment of this invention prior to insertion of the needle and catheter into a patient;

FIG. 4 is a side view in cross-section of the first embodiment of this invention with the needle in the retracted position after the catheter has been advanced into a patient;

FIG. 6 is a perspective view of a second embodiment of this invention with the catheter advanced over the needle prior to retraction of the needle into the barrel;

FIG. 7 is a side view in cross-section of the second embodiment of this invention prior to insertion of the needle and catheter into a patient;

FIG. 8 is a side view in cross-section of the second embodiment of this invention with the needle in the retracted position after the catheter has been advanced into a patient;

FIG. 9 is a side view in cross-section of a third embodiment of this invention prior to insertion of the needle and catheter into a patient;

FIG. 10 is a side view in cross-section of the third embodiment of this invention with the catheter advanced over the needle prior to retraction of the needle into the barrel;

FIG. 20 is a side view in cross-section of the distal portion of the fifth embodiment of the invention prior to insertion of the needle and catheter into a patient;

FIG. 21 is a side view in cross-section of the distal portion of the fifth embodiment of the invention after the catheter has been advanced over the needle and the needle is being withdrawn into the barrel;

FIG. 22 is a perspective view of the proximal end of the camming rod and the keylatch of the fifth embodiment of the invention, with the keylatch shown at the extreme proximal end of the camming rod in phantom;

FIG. 23 is a perspective view similar to FIG. 22 but showing a variation of the camming rod and the keylatch.

DETAILED DESCRIPTION OF THE INVENTION

Figure 1:
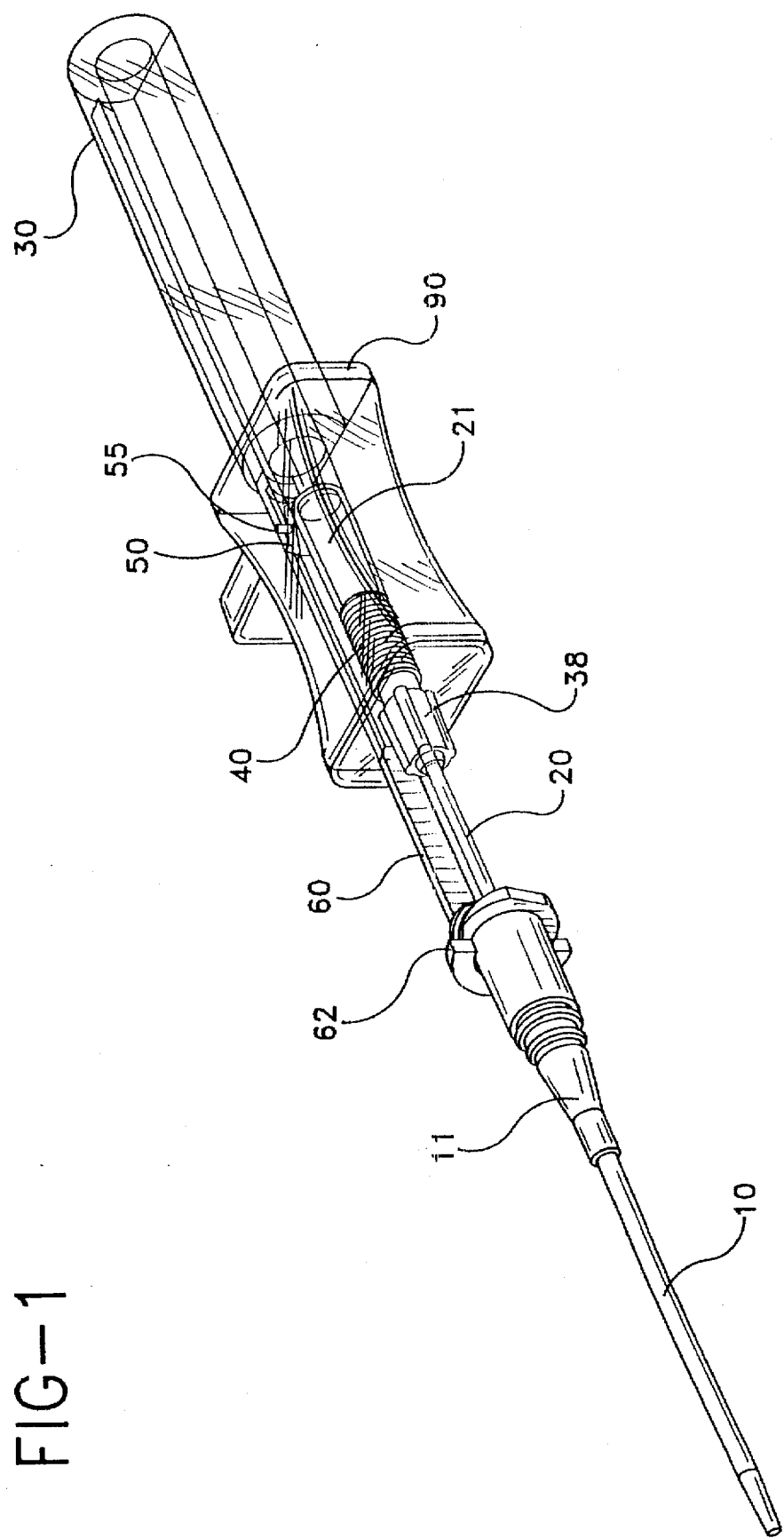
FIG. 1 is a perspective view of a first embodiment of this invention with the catheter advanced from the distal end of the barrel and the needle in the fully extended position prior to retraction into the barrel.

One embodiment of the catheter-advancement actuated needle retraction system of this invention can be seen generally in FIGS. 1 through 5. This system includes a catheter 10, a catheter hub 11, a needle 20, a needle hub 21, which can include a flashback chamber, a barrel 30 for shielding the sharp distal tip of needle 20 after use, a spring 40, a movable latch 50 and a latch actuator 60. Barrel 30 can include a contoured ergonomic handle 90 for ease of gripping.

Referring to FIGS. 3 and 4, barrel 30 is generally hollow and has an inner longitudinally extending wall 31 that divides barrel 30 into two distinct chambers. This wall 31 serves to guide needle hub 21 within barrel 30 as needle hub 21 and needle 20 are retracted into barrel 30 under the force of spring 40 In addition, wall 31 helps to avoid interference between latch actuator 60 and needle hub 21 during operation of the mechanism. Of course, it is not essential to have wall 31 and two distinct chambers. However, this configuration facilitates reliable retraction of needle 20 into barrel 30. Wall 31 should define a cut out portion to allow placement of a latch 50 therein. The purpose and description of latch 50 will be provided hereinafter.

First chamber 32 houses needle hub 21, spring 40 and needle 20 when it is retracted into barrel 30. First chamber 32 should be long enough so that when needle hub 21 is completely retracted into barrel 30 so needle hub 21 is adjacent to the proximal end of barrel 30, the sharp distal tip of needle 20 does not extend beyond the distal end of barrel 30. The distal end of first chamber 32 includes an opening to allow needle 20 to extend beyond the distal end of barrel 30. The distal end of barrel 30 includes a neck 38. Neck 38 has a proximal end around which spring 40 can be located and a distal end around which catheter hub 11 can be placed. Alternatively, instead of forming the distal end of barrel 30 to have neck 38, needle hub 21 could include a distal neck substantially in the shape of the distal portion of neck 38. This distal neck of needle hub 21 would then extend through an opening in the distal wall of barrel 30 sized to fit that portion of needle hub 21. The portion of needle hub 21 proximal to its distal neck would have to include a cut out portion or otherwise be sized to accommodate spring 30. Spring 40 would then surround that portion of needle hub 21 and abut the distal wall around the opening formed in barrel 30 for the distal neck of needle hub 21.

Second chamber 33 houses latch actuator 60 and should be sized accordingly. The distal end of second chamber 33 includes an opening through which latch actuator 60 can extend.

Needle 20 is attached at its proximal end to needle hub 21. Needle hub 21 preferably includes a flashback chamber to collect the blood that "flashes back" through needle 20 when the sharp distal tip of needle 20 pierces a patient's vein. The combined length of needle 20 and needle hub 21 should be less than the internal length of barrel 30. In this way, and as discussed above, when needle 20 and needle hub 21 are retracted into first chamber 32 of barrel 30, the sharp distal tip of needle 20 will not be exposed outside of barrel 30 but instead will be safely housed inside.

Spring 40 is disposed about the proximal portion of neck 38 between the distal end of needle hub 21 and the distal wall of barrel 30. Although spring 40 is preferably placed coaxially about the proximal portion of neck 38, spring 40 could also be located adjacent to neck 38 or in some other non-coaxial arrangement with the proximal portion of neck 38. When needle 20 is in the extended position, the distal end of needle hub 21 is adjacent to the distal wall of barrel 30. Spring 40 is placed in compression in this arrangement. Thus needle hub 21, and needle 20, will be urged away from the distal end of barrel 30 by spring 40 if needle hub 21 is not held in position. Although this is the preferred orientation for spring 40 in this embodiment as well as the remaining embodiments of this invention, it is to be understood that spring 40 could be located between and connected to the proximal end of barrel 30 and the proximal end of needle hub 21. By placing spring 40 in tension in this arrangement, a biasing force is provided to needle hub 21 to urge needle 20 toward the proximal end of barrel 30. This arrangement can also be used with the other embodiments of this invention.

Latch 50 serves to maintain the position of needle hub 21 adjacent to the distal end of barrel 30 during insertion of catheter 10 into a patient. Latch 50 is secured to barrel 30 such that it pivots about pin 55. Latch 50 includes two generally parallel teeth 51 and 52 extending in opposite directions from either end of the body of latch 50. First tooth 52 is configured to engage the proximal end of needle hub 21 to maintain the position of needle hub 21 adjacent to the distal wall of barrel 30 Latch 50 may be pivoted in a counterclockwise direction as shown in FIGS. 3 and 4 to allow spring 40 to urge needle hub 21 and needle 20 away from the distal wall of barrel 30 to retract needle 20 into first chamber 32 of barrel 30 and thus shield the sharp distal tip of needle 20 after use.

Figure 2:
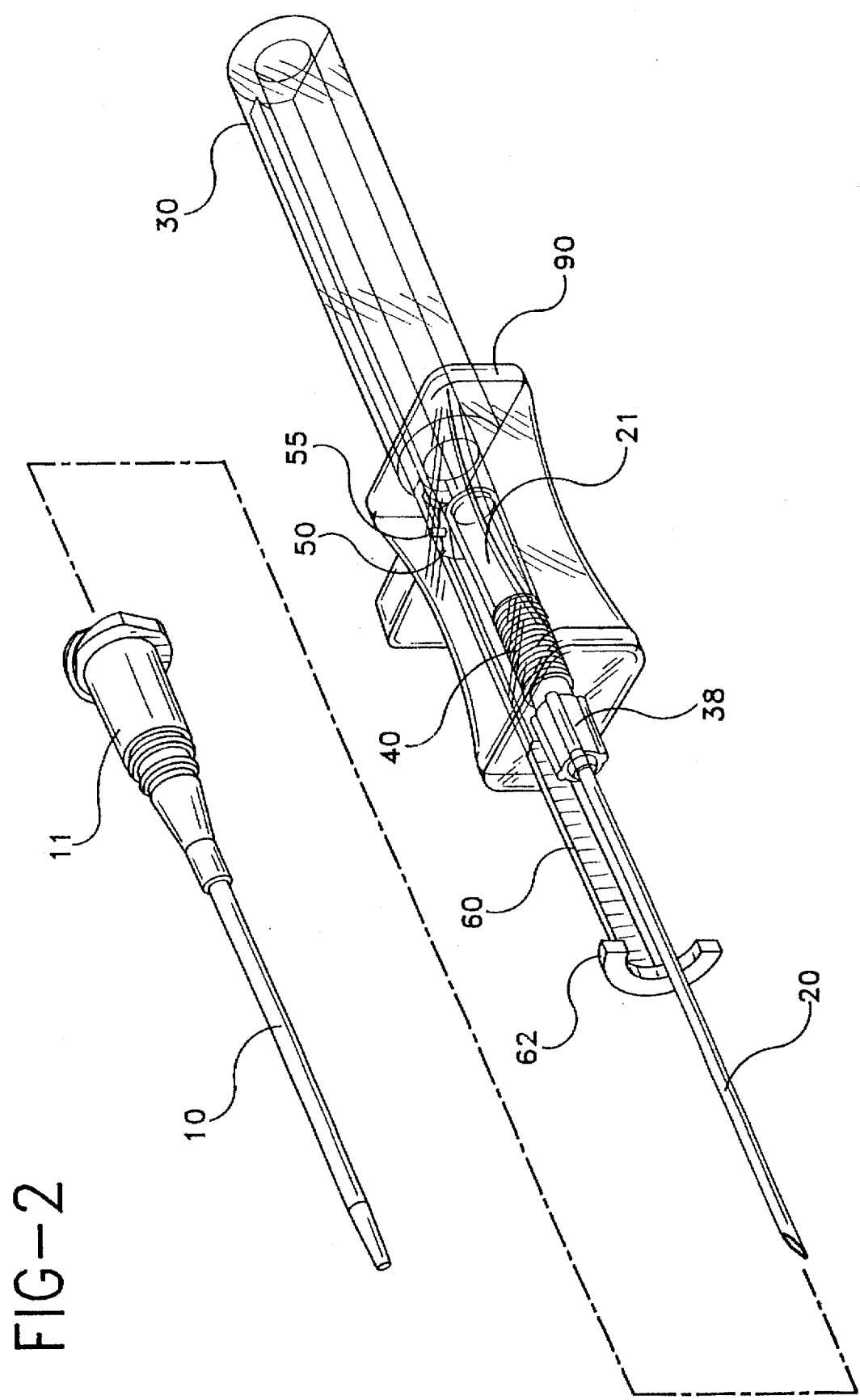
FIG. 2 is a perspective view of the first embodiment of the invention similar to that shown in FIG. 1 but with the catheter removed from the introducer needle assembly for clarity.

Latch actuator 60 is used to pivot latch 50 away from engagement with needle hub 21. Latch actuator 60 has a first shoulder 61 at its proximal end that engages with second tooth 51 as latch actuator 60 is moved in the distal direction to rotate latch 50 in the counterclockwise direction as seen in FIGS. 3 and 4. Latch actuator 60 has a second shoulder 62 at its distal end that engages catheter hub 11. As seen in FIGS. 1 and 2, second shoulder 62 can take the form of a semi-circular clip that connects to catheter hub 11 adjacent to the proximal flange of catheter hub 11. Once needle 20 and catheter 10 have properly engaged a patient's vein, the health care worker can advance catheter 10 or retract barrel 30 to remove needle 20 from catheter 10. As a result of this motion, latch actuator 60 moves distally with respect to barrel 30 since second shoulder 62 of latch actuator 60 is still held to catheter hub 11. Shoulder 61 thus moves toward the distal wall of barrel 30 and engages second tooth 51 to pivot latch 50 away from needle hub 21. Spring 40 will then cause needle 20 to be retracted into barrel 30. At this point, second shoulder 62 can be moved away from contact with catheter hub 11. The needle assembly can then be completely withdrawn leaving catheter 10 in place.

Figure 5:
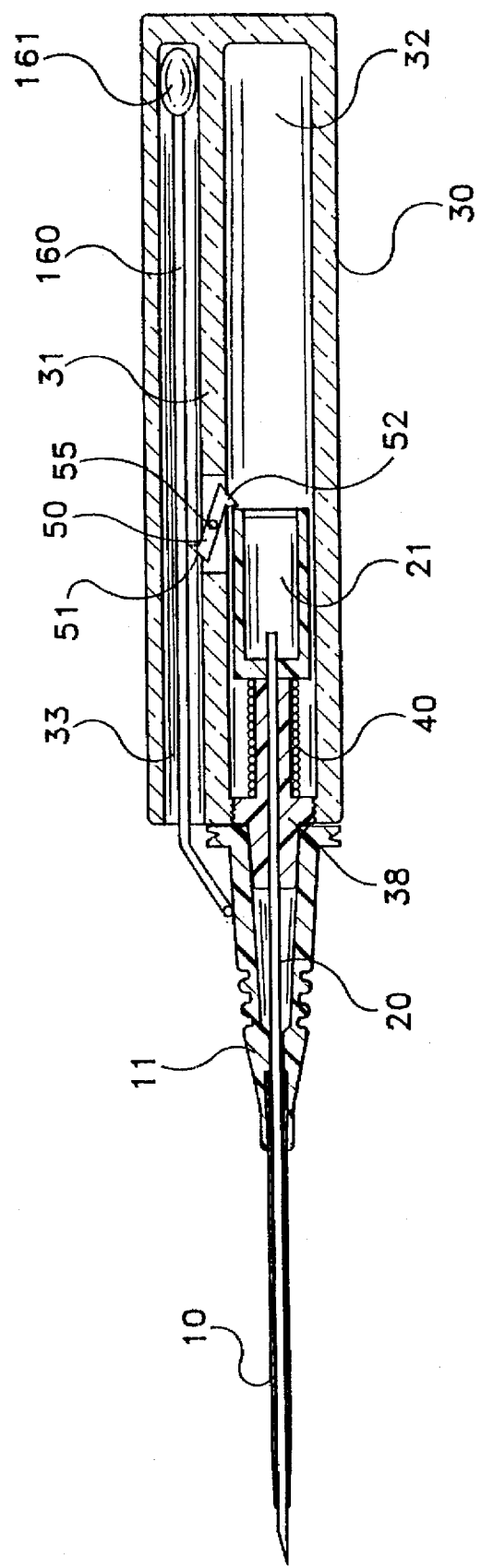
FIG. 5 is a side view similar to FIG. 3 but showing a variation of the first embodiment of the invention with a different latch actuator.

As an alternative embodiment, latch actuator 160 can be connected to catheter hub 11 as shown in FIG. 5 by any standard means. In addition, an enlarged bead 161 or some other protuberance at the proximal end of latch actuator 160 can be used instead of a shoulder to engage second tooth 51 of latch 50.

A second embodiment of latch actuator 260 is shown in FIGS. 6 through 8. In that embodiment, latch actuator 260 comprises a wire formed into two longitudinally extending rails 269 and a push off tab 268. Alternatively, latch actuator 260 could include only one longitudinally extending rail 269. Push off tab 268 is formed such that it snaps over catheter hub 11 and can be easily removed from catheter hub 11 once catheter 10 is properly placed in a patient's vein. Longitudinally extending rails 269 extend into barrel 230 in chambers 231 and 232 so that at least one of the longitudinally extending rails 269 will interact with latch 250 to disengage latch 250 from needle hub 221 to allow needle 20 to retract into barrel 230.

In the second embodiment of this invention, latch 250 pivots about point 251 in a cantilever fashion and is biased away from needle hub 221. Latch 250 includes an enlarged foot 252 than engages needle hub 221. Foot 252 is held in slot 225 of needle hub 221 by one of the longitudinally extending rails 269. See FIG. 7. Thus, when needle 20 is withdrawn from catheter 10 or when catheter 10 is advanced further into a patient's vein, the longitudinally extending rail that holds foot 252 in slot 225 will move away from engagement with foot 252. With nothing holding foot 252 in slot 225 against its bias, foot 252 will move away from slot 225. This will allow spring 40 to urge needle hub 221 and thus needle 20 away from the distal end of barrel 230.

FIGS. 7 and 8 also show another configuration for the proximal end of barrel neck 238 and the distal end of needle hub 221. As can be seen, a cut out exists in the proximal end of barrel neck 238 and the distal end of needle hub 221 to house the ends of spring 40.

Figure 15:
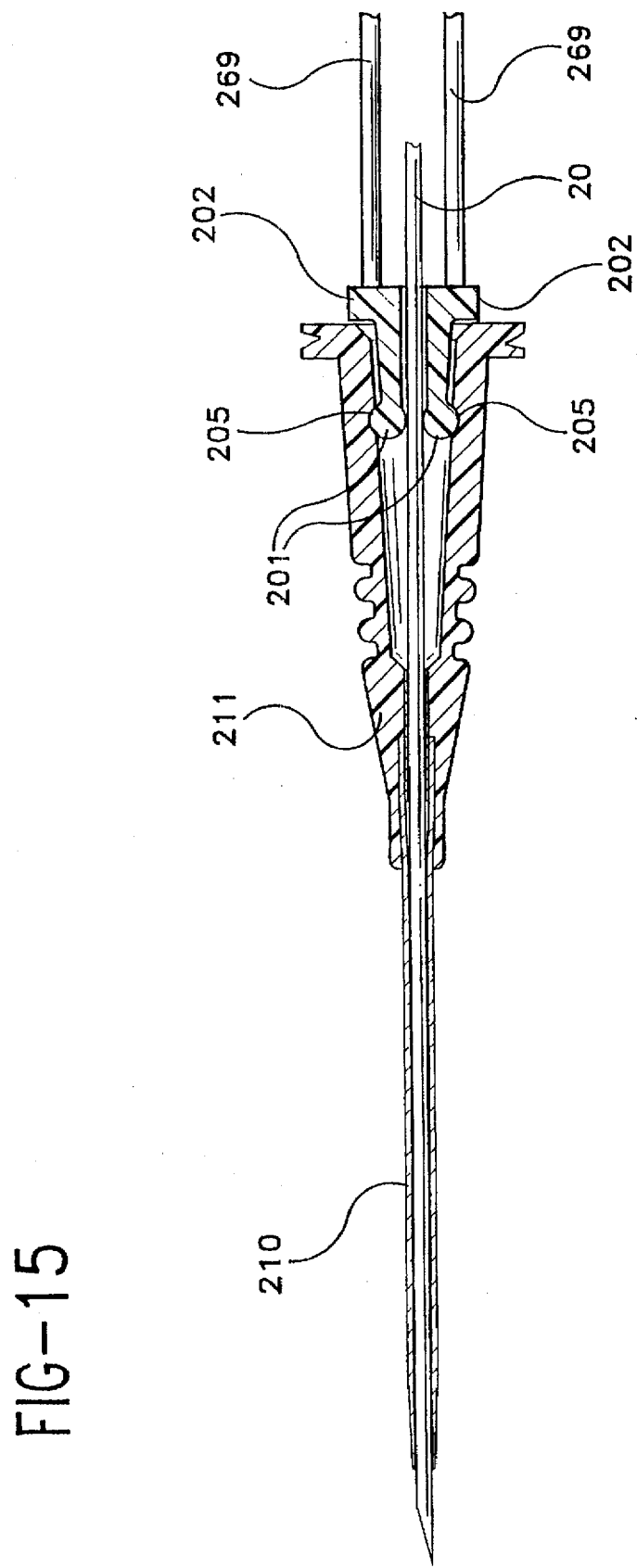
FIG. 15 is a side view in cross-section of an alternative embodiment of the catheter hub and distal portion of the latch actuator of this invention.

As an alternative to push off tab 268 shown in the embodiment of FIGS. 6 through 8, an automatic release mechanism such as shown in FIG. 15 can be used. In the version of FIG. 15, each longitudinally extending rail 269 is formed to have a bulbous distal tip 201 and an outwardly extending shoulder 202 along its distal portion proximal of bulbous distal tip 201. These bulbous distal tips 201 are dimensioned such that they can fit within the proximal end of catheter hub 211. Each bulbous distal tip 201 fits inside a cut out portion 205 on the inside of catheter hub 211. Shoulders 202 abut the proximal flange of catheter hub 211. With needle 20 extending through catheter 210, rails 269 are biased into engagement with cut out portions 205 of catheter hub 211. When catheter 210 is advanced to actuate the latch, needle 20 is withdrawn from catheter 210 and catheter hub 211 thus removing the biasing force for rails 269. Bulbous distal tips 201 of rails 269 thus lose contact with cut out portions 205 of catheter hub 211 allowing catheter 210 and catheter hub 211 to be automatically removed from the introducer needle assembly. It is to be understood that the automatic release mechanism shown in FIG. 15 could be adapted for use with all of the embodiments of the invention disclosed herein.

Figure 11:
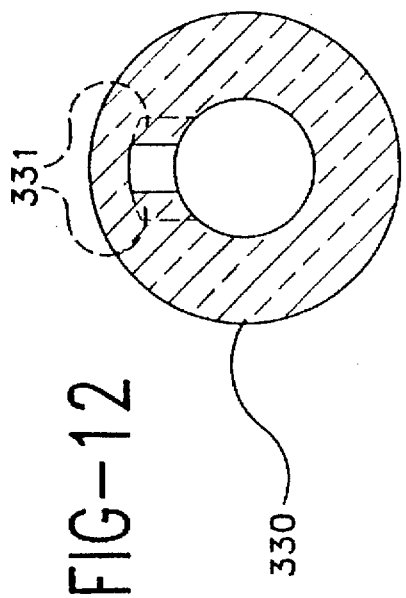
FIG. 11 is a cross-sectional view of the third embodiment of this invention taken along line 11—11 in FIG. 10.
Figure 12:
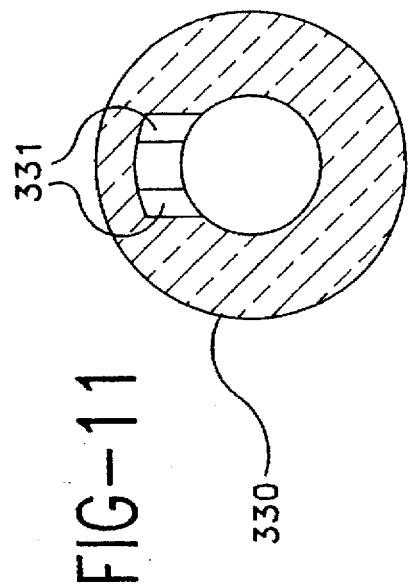
FIG. 12 is a cross-sectional view of the third embodiment of this invention taken along line 12—12 in FIG. 10.
Figure 14:
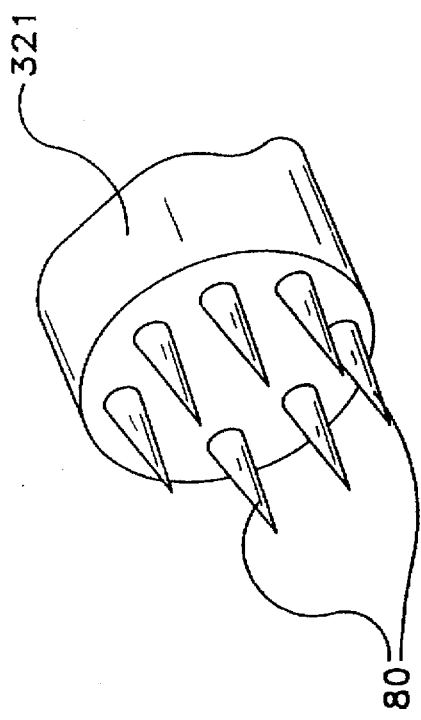
FIG. 14 is a perspective view of the proximal end of the needle hub shown in FIG. 13.
Figure 13:
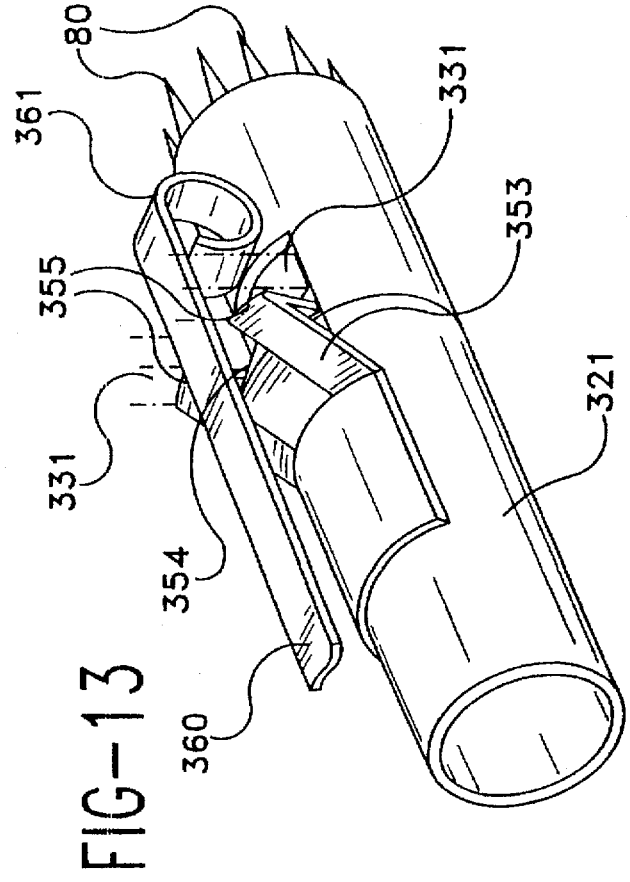
FIG. 13 is a perspective view of the needle hub used in the third embodiment for this invention.

In the third embodiment of this invention shown in FIGS. 9 through 14, latch 350 is affixed to the outer surface of needle hub 321. Latch 350 has an upwardly extending body 353 that is biased away from needle hub 321 Latch 350 also has a portion which descends from body 353 in a gradual ramp 354 and another portion which ends in abutments 355 These abutments 355 engage with shoulders 331 formed in the inner wall of barrel 330. Shoulders 331 are shown in FIGS. 11 and 12 and are in phantom in FIG. 13.

Latch actuator 360 is formed with a pigtail 361 at its proximal end. Needle hub 321 is oriented in barrel 330 so that latch actuator 360 extends over ramp 354 of latch 350. As needle 20 is removed from catheter 10, latch actuator 360 passes over ramp 354. When pigtail 361 passes over ramp 354, latch 350 is urged toward needle hub 321 so that abutments 355 disengage from shoulders 331. This allows spring 40 to urge needle hub 321 away from the distal wall of barrel 330.

The proximal end of needle hub 321 can also include a plurality of longitudinally extending tines 80. Tines 80, which may be collapsible, cushion needle hub 321 when it is forced against the proximal wall of barrel 330. These tines 80 could also be incorporated on the needle hubs in all of the different embodiments of this invention as well as in different safety catheter systems that use a spring to retract the needle inside the barrel, such as described in U.S. Pat. No. 4,747,831.

Figure 16:
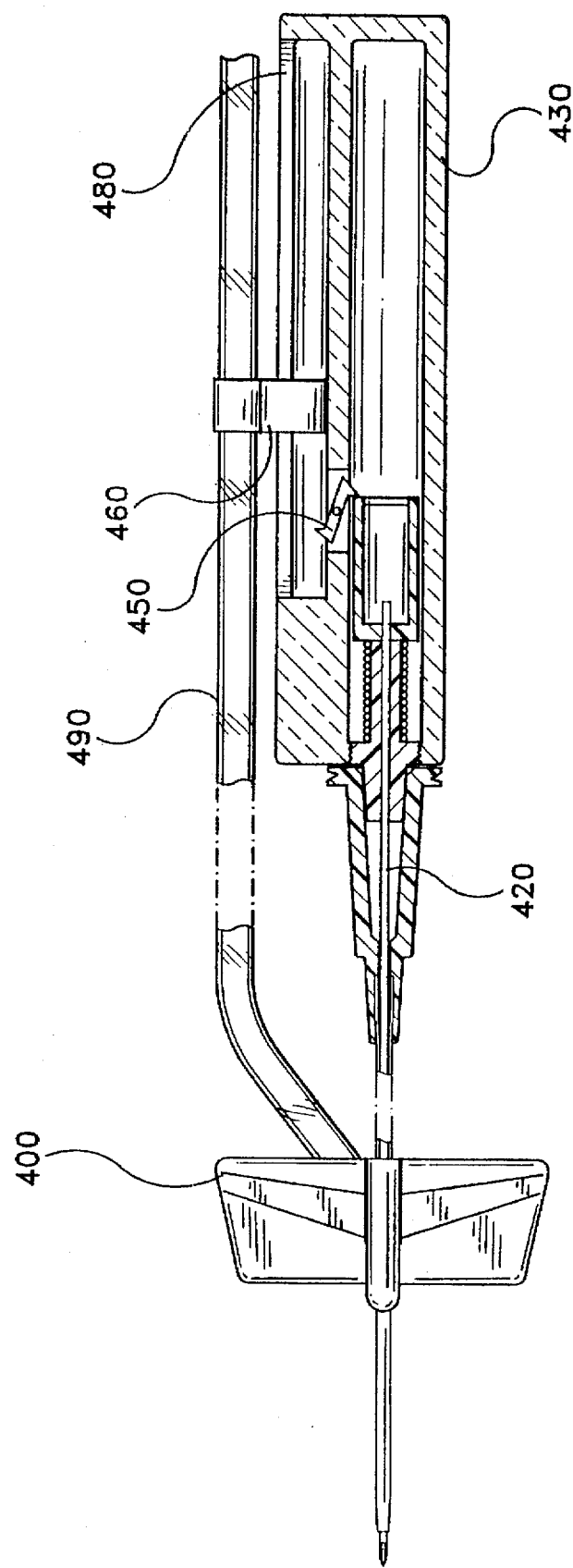
FIG. 16 is a side view in cross-section of a fourth embodiment of this invention for use with a winged catheter.

A variation of the first embodiment of this invention is shown in the fourth embodiment of FIG. 16. The catheter-advancement actuated needle retraction system of this invention can be used with a butterfly type catheter 400 having an extension tube 490 connected thereto to facilitate the infusion of I.V. fluids into the patient. In this embodiment, a tab 460 is affixed to extension tube 490 and extends into barrel 430 through a slot 480 formed in the side wall of barrel 430. As barrel 430 is moved away from catheter 400 to remove needle 420, tab 460 slides distally along slot 480 to actuate latch 450. Tab 460 can be connected to extension tube 490 via a removable clip. Alternatively, tab 460 can be formed with a score line or some other means for weakening the connection between tab 460 and extension tube 490 to allow tab 460 to be removed easily therefrom.

In the fifth embodiment of this invention shown in FIGS. 17 through 24, a camming rod 569 is used to move a keylatch 550 out of engagement with needle hub 521. Keylatch 550 includes a keyhole 555 therein having a larger portion 555a and a smaller portion 555b. Keylatch 550 rides along rail 595 of camming rod 569. Rail 595 is arranged to allow either larger hole 555a or smaller hole 555b to be aligned with the longitudinal axis of camming rod 569.

Figure 17:
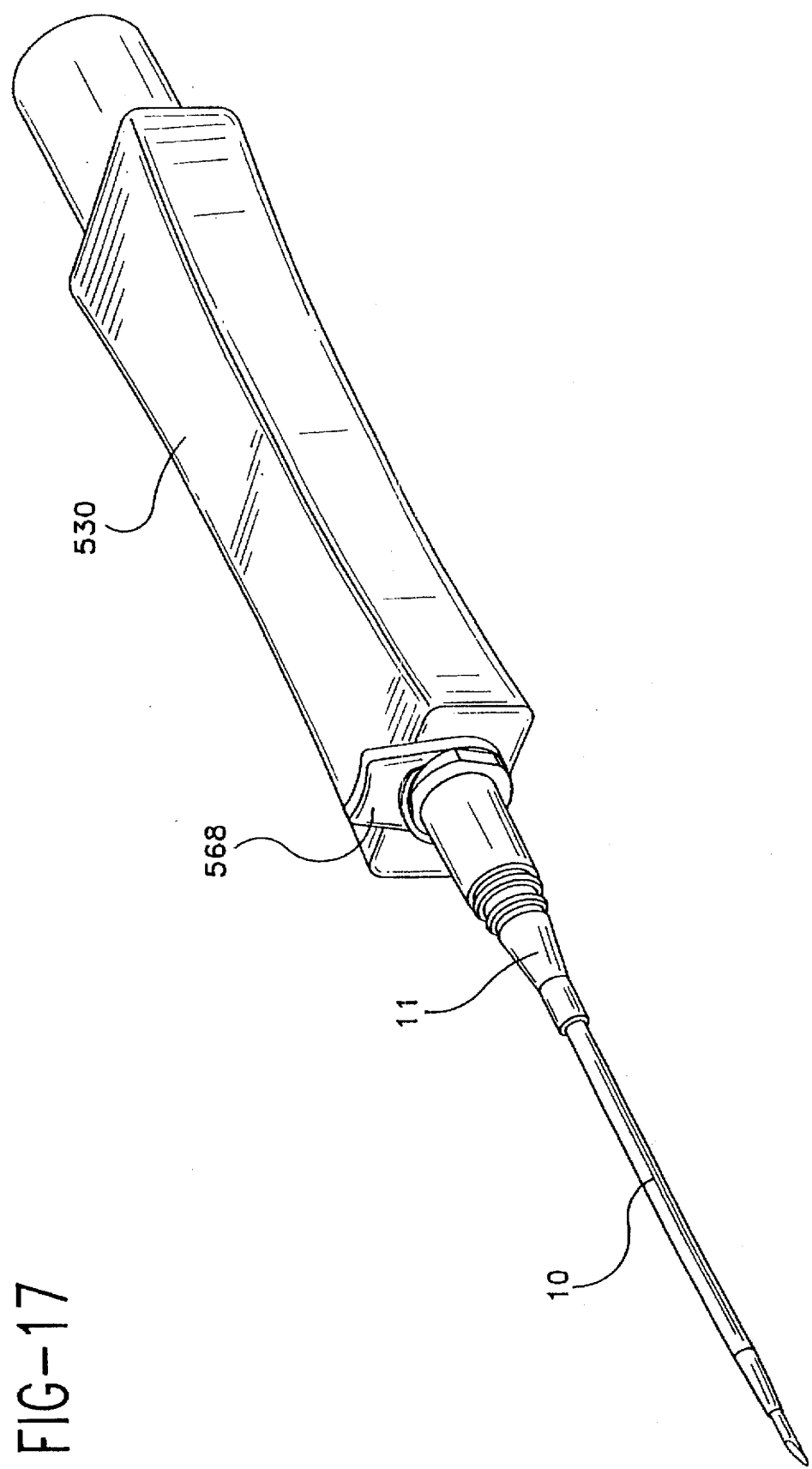
FIG. 17 is a perspective view of a fifth embodiment of this invention prior to insertion of the needle and catheter into a patient.
Figure 18:
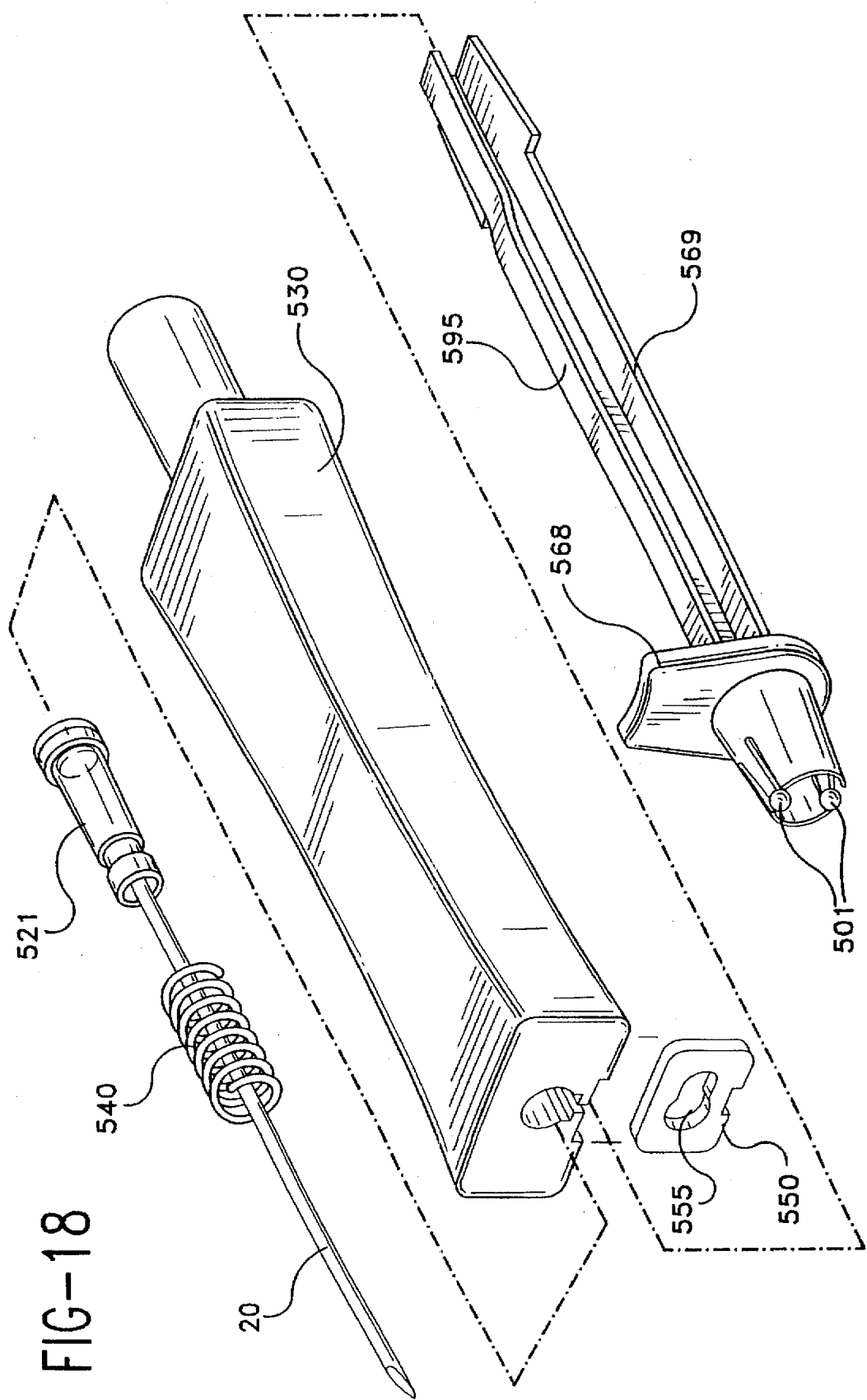
FIG. 18 is an exploded perspective view of the fifth embodiment of this invention.
Figure 19:
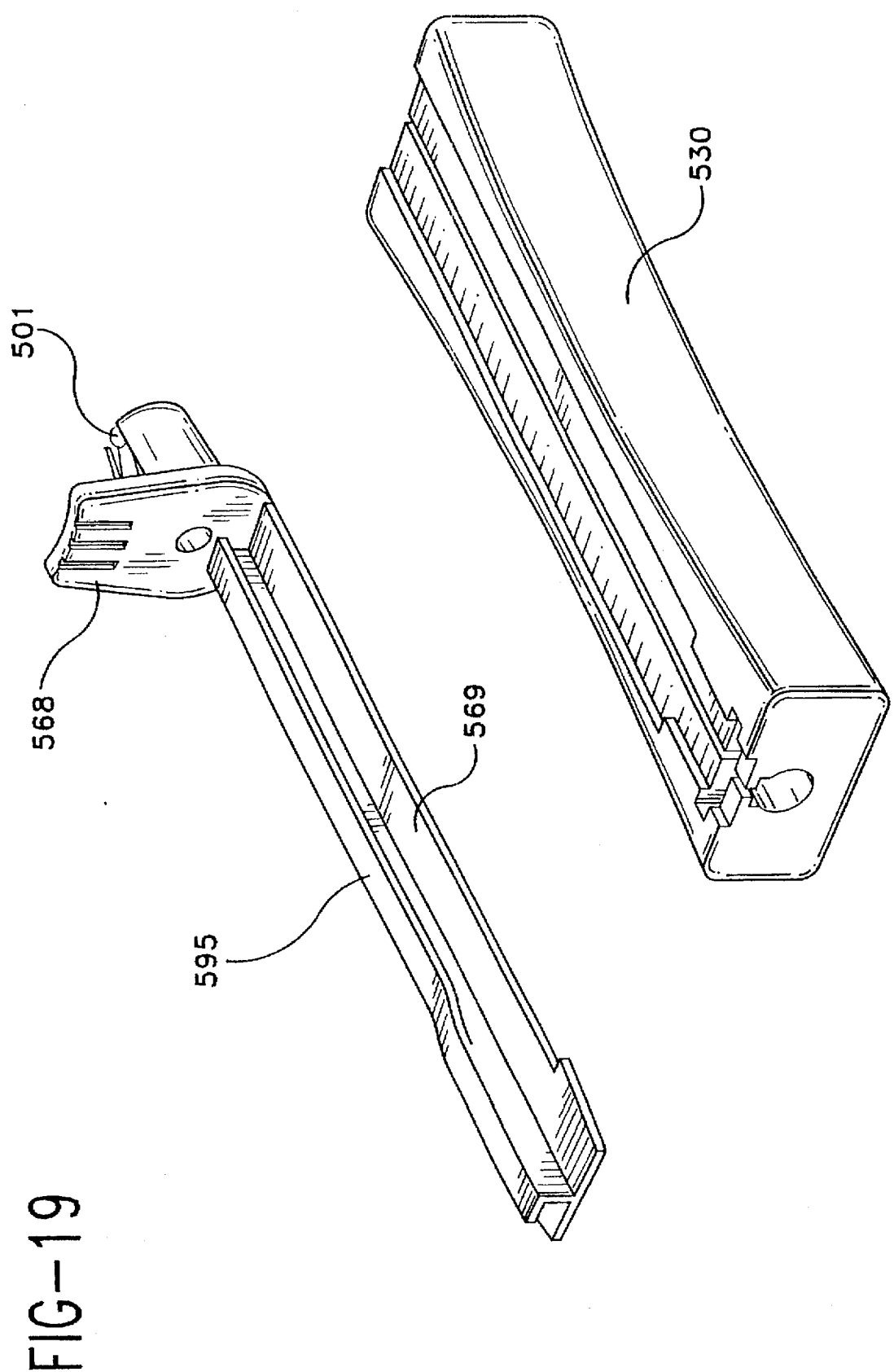
FIG. 19 is a perspective view of the rear of the camming rod and of the front and bottom of the barrel of the fifth embodiment of this invention.

Camming rod 569 rides along the bottom of barrel 530 so that push off tab 568 is either adjacent to the distal end of barrel 530, as shown in FIGS. 17, and 20, or is removed therefrom as shown in FIG. 21. The distal end of camming rod 269 includes bulbous distal tips 501 which function in the same manner as the automatic release mechanism shown in FIG. 15.

Keylatch 550 is disposed inside barrel 530 about needle hub 521. When camming rod 569 is in the position shown in FIGS. 17 and 20, smaller hole 555b engages needle hub 521 to hold it adjacent to the distal end of barrel 530. In this position spring 540 is held in compression between keylatch 550 and the proximal end of needle hub 521. After the tip of needle 20 and catheter 210 have been inserted into a patient, push off tab 568 can be pushed forwardly to advance catheter 210 further into the patient. This motion advances camming rod 569 forwardly with respect to barrel 530. This in turn causes keylatch 550 to be moved to the side because of the orientation of rail 595 until larger hole 555a is aligned with the longitudinal axis of camming rod 569. Larger hole 555a has a sufficiently large diameter to allow needle hub 521 to pass therethrough. Thus when camming rod 569 is advanced larger hole 555a of keyhole latch 550 becomes aligned with needle hub 521 to allow spring 540 to urge needle hub 521 to the proximal end of barrel 530 and retract needle 20.

Keyhole latch 550 and rail 595 can have different orientations, as shown in FIG. 23, as long as keylatch 550 maintains needle hub 521 adjacent to the distal end of barrel 530 against the force of spring 540, and keylatch 550 can be selectively moved to allow needle hub 521 to be moved to the proximal end of barrel 530 by the force of spring 540. In the version shown in FIG. 23, rail 595 is oriented to move keylatch 550 vertically. In this version keyhole 555 has larger opening 555a beneath smaller opening 55b so that as rail 595 is moved forwardly, larger opening 555a will be moved upwardly into alignment with needle hub 521.

Figure 24:
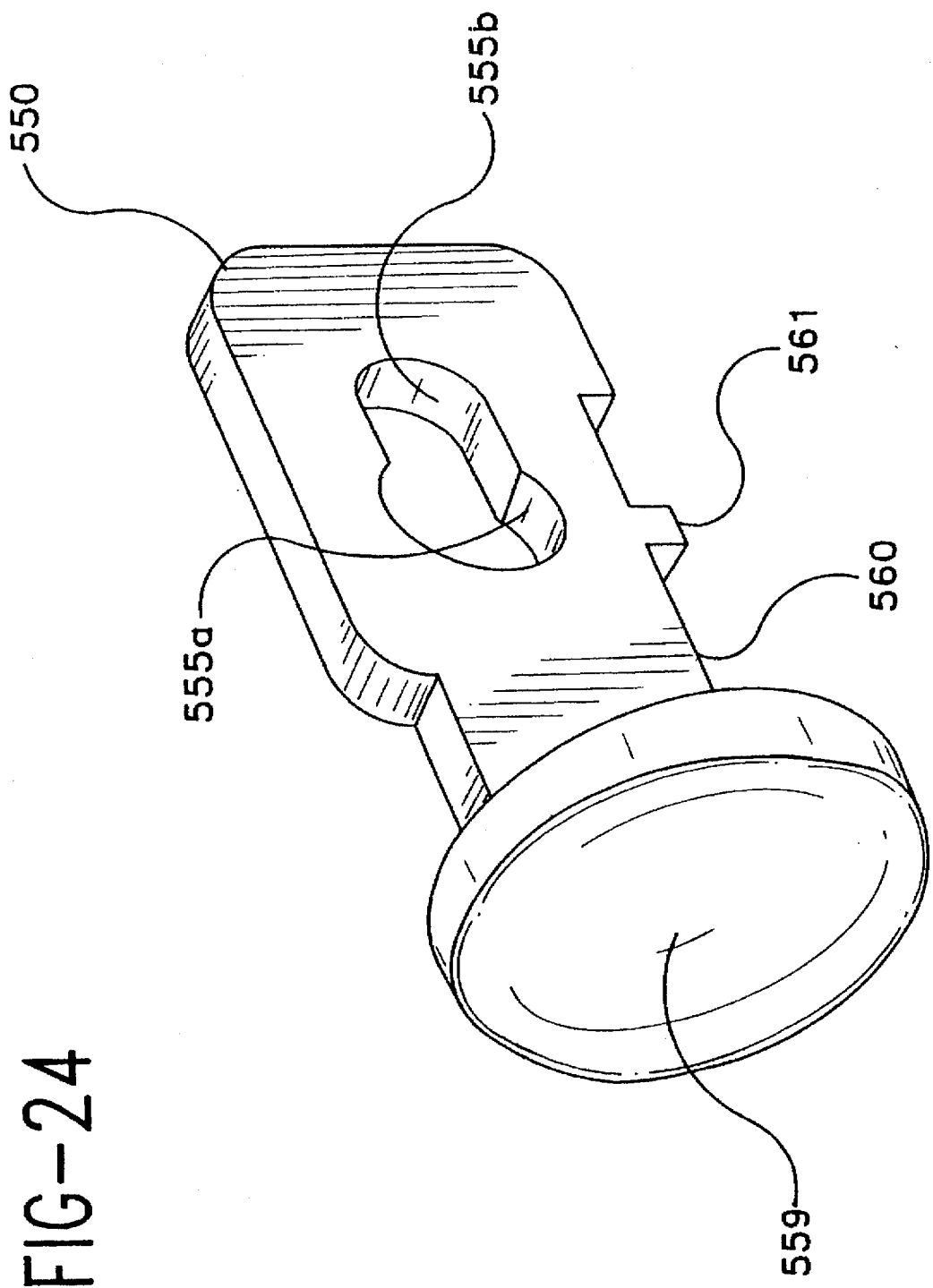
FIG. 24 is a perspective view of another embodiment of the keylatch.

As shown in FIG. 24, keylatch 550 can include a pushing surface 559 that extends outs,do of barrel 530 and a cutout portion 560 float defines a breakable pin 561. This embodiment allows keylatch 550 to be activated to retract needle 20 into barrel 530 without the need to advance camming rod 569.

Each of these embodiments achieves the desired goal of providing a safety catheter and needle introducer assembly where the needle can be covered after use and which is easy to use.

What is claimed is:

1. A catheter and needle introducer assembly, comprising:

a barrel defining a barrel lumen and having a proximal end and a distal end, the distal end defining a distal wall with an opening extending therethrough;

a catheter having a proximal end and a distal end;

a catheter hub, having an inner wall, affixed to the proximal end of the catheter;

a needle having a sharp distal tip and a proximal end;

a needle hub having a proximal end and a distal end affixed to the proximal end of the needle, the needle hub being disposed in the barrel lumen such that the sharp distal tip of the needle initially extends distally of the distal wall of the barrel through the opening coaxially within the catheter and the catheter hub with the catheter hub adjacent to the distal wall of the barrel;

a spring disposed in the barrel lumen and operatively engaged with the needle hub to urge the needle hub toward the proximal end of the barrel;

a means for retaining the needle hub adjacent to the distal end of the barrel wherein the means for retaining engages the needle hub to retain the needle hub adjacent to the distal end of the barrel; and a means removably engaged with the catheter hub and movable distally with respect to the proximal end of the barrel in order to move the means for retaining the needle hub adjacent to the distal end of the barrel out of engagement with the needle hub to allow the spring to force the needle hub toward the proximal end of the barrel when the catheter hub is moved distally from the distal wall of the barrel.

2. The catheter and needle introducer assembly of claim 1 further comprising a means for cushioning the proximal end of the needle hub when the needle hub is retracted against the proximal end of the barrel.

3. The catheter and needle introducer assembly of claim 2 wherein the means for cushioning includes a plurality of tines longitudinally extending from the proximal end of the needle hub.

4. The catheter and needle introducer assembly of claim 3 wherein the tines are collapsible.

* * * * *